(12) United States Patent
Urich et al.

(10) Patent No.: US 8,092,427 B2
(45) Date of Patent: Jan. 10, 2012

(54) ASPIRATION SYSTEM FOR OPHTHALMIC MEDICAL DEVICES

(75) Inventors: Alex Urich, Rancho Santa Margarita, CA (US); Armand Maaskamp, Coto de Caza, CA (US)

(73) Assignee: Data, LLC, Irvine, CA (US)

( * ) Notice: Subject to any disclaimer, the term of this patent is extended or adjusted under 35 U.S.C. 154(b) by 1333 days.

(21) Appl. No.: 11/336,504

(22) Filed: Jan. 19, 2006

(65) Prior Publication Data

US 2006/0173404 A1    Aug. 3, 2006

Related U.S. Application Data

(63) Continuation-in-part of application No. 11/305,586, filed on Dec. 16, 2005, now abandoned, which is a continuation-in-part of application No. 11/196,044, filed on Aug. 2, 2005, which is a continuation-in-part of application No. 11/186,029, filed on Jul. 20, 2005, now abandoned.

(60) Provisional application No. 60/610,846, filed on Sep. 16, 2004.

(51) Int. Cl.
*A61M 1/00* (2006.01)
*A61B 17/20* (2006.01)

(52) U.S. Cl. .......................................... 604/118; 604/22

(58) Field of Classification Search .................... 604/22, 604/118–121
See application file for complete search history.

(56) References Cited

U.S. PATENT DOCUMENTS

| 5,173,196 | A | * | 12/1992 | Macrae .......................... 210/808 |
| 5,807,353 | A | | 9/1998 | Schmitz |
| 5,954,692 | A | | 9/1999 | Smith et al. |
| 6,478,781 | B1 | | 11/2002 | Urich et al. |
| 6,585,708 | B1 | | 7/2003 | Maaskamp |
| 6,599,271 | B1 | | 7/2003 | Easley |
| 6,780,166 | B2 | | 8/2004 | Kanda et al. |
| 7,083,591 | B2 | | 8/2006 | Cionni |
| 2002/0022810 | A1 | | 2/2002 | Urich |
| 2002/0124346 | A1 | | 9/2002 | Steiner et al. |
| 2002/0128560 | A1 | * | 9/2002 | Urich ............................ 600/500 |
| 2004/0069714 | A1 | | 4/2004 | Ferguson |
| 2004/0089592 | A1 | * | 5/2004 | Shechter et al. .............. 210/150 |
| 2005/0159758 | A1 | | 7/2005 | Laks |
| 2006/0058728 | A1 | | 3/2006 | Urich |
| 2006/0058729 | A1 | | 3/2006 | Urich |
| 2006/0173426 | A1 | | 8/2006 | Urich et al. |

* cited by examiner

*Primary Examiner* — Nicholas Lucchesi
*Assistant Examiner* — Victoria P Campbell
(74) *Attorney, Agent, or Firm* — Barcelo, Harrison & Walker LLP; Joshua C. Harrison, Esq.

(57) ABSTRACT

An ophthalmic aspiration system that can be used with a hand piece and a vacuum source, is disclosed and claimed. The aspiration system includes a first tube that is connected to the hand piece and a second tube that is connected to a vacuum source. A filter assembly is connected to both tubes to filter out particles aspirated into the system. The second tube has an inner diameter smaller than an inner diameter of the first tube. The smaller second tube limits the amount of flow through the system to minimize vacuum surges caused by occlusions.

16 Claims, 3 Drawing Sheets

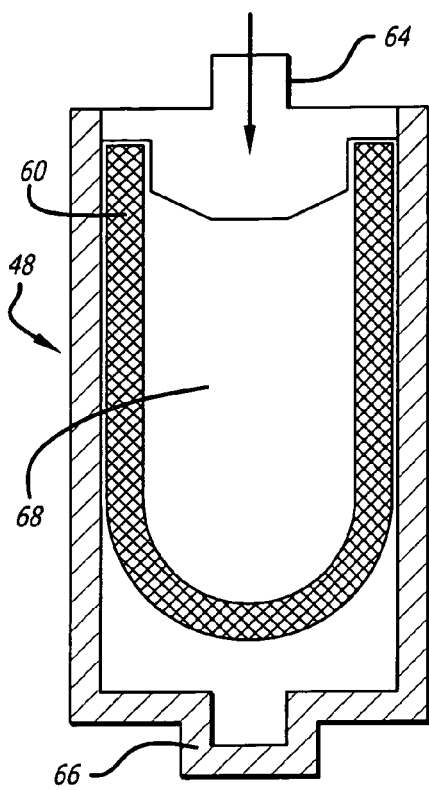
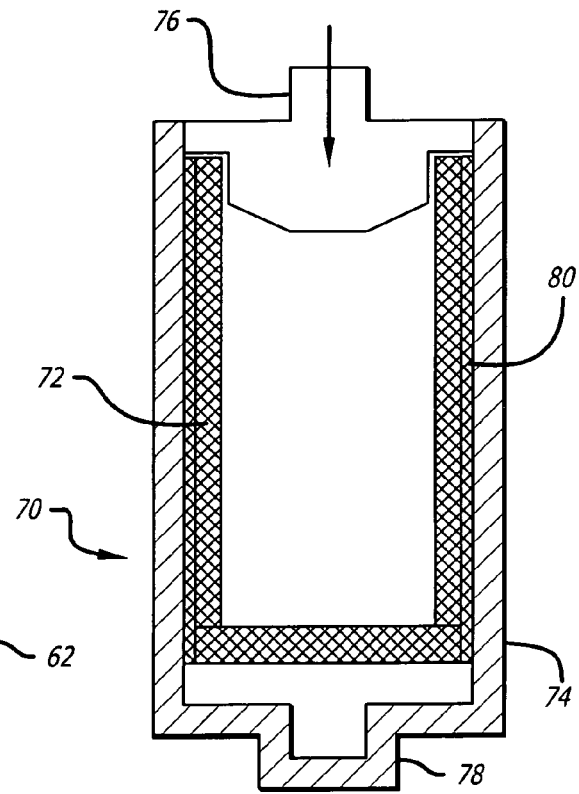
FIG. 2
FIG. 4
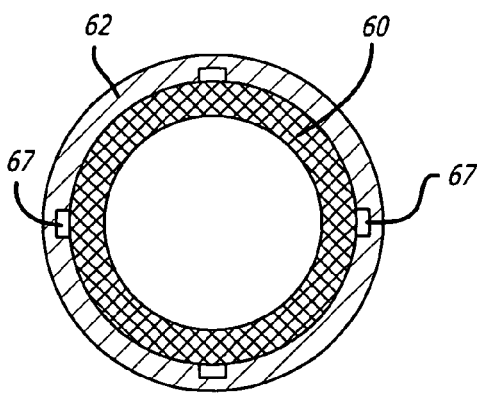
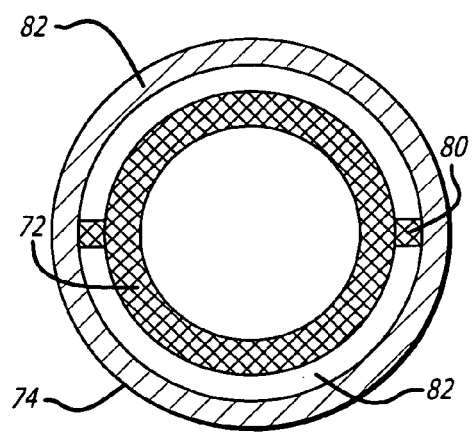
FIG. 3
FIG. 5

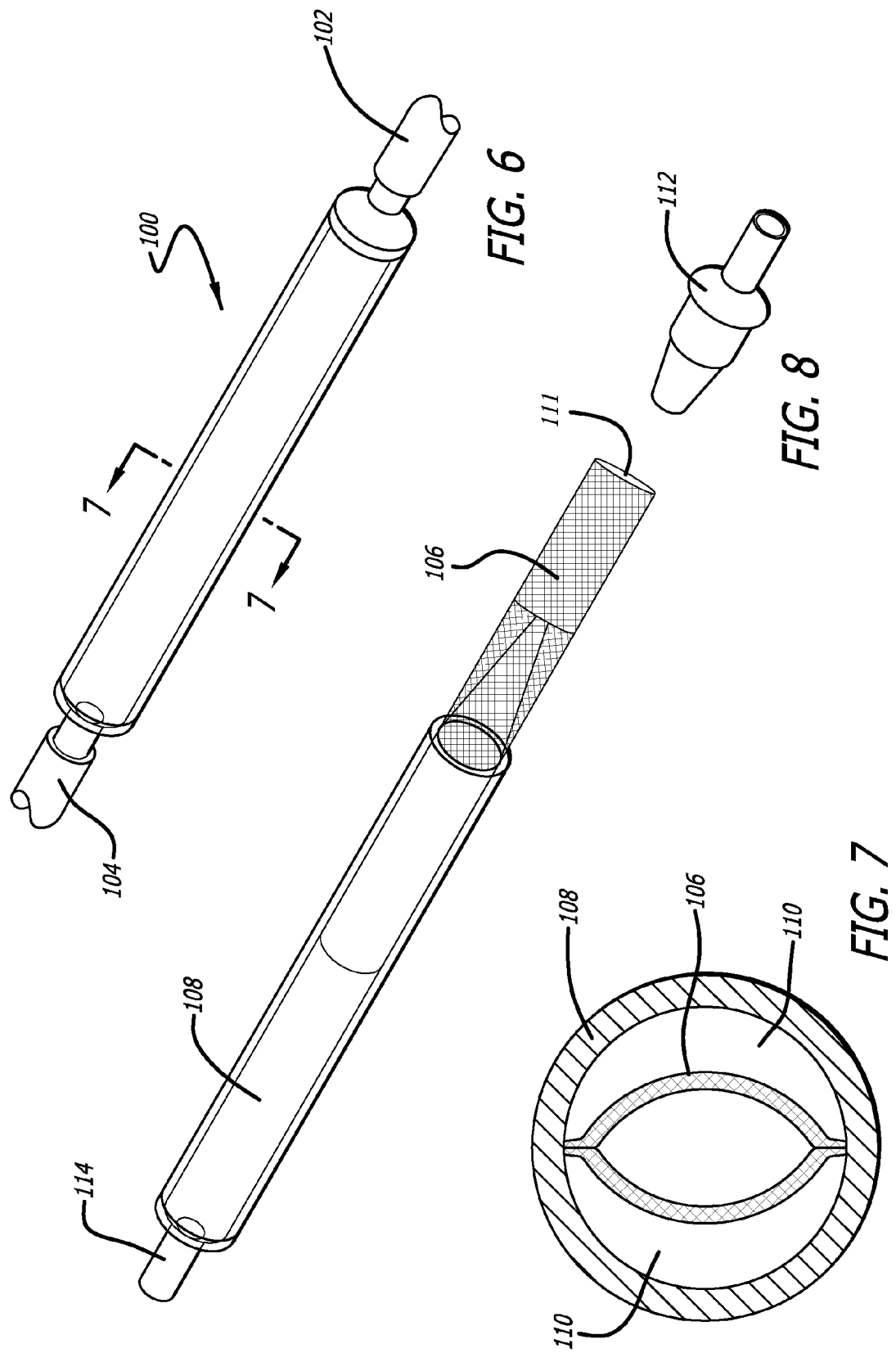

ASPIRATION SYSTEM FOR OPHTHALMIC MEDICAL DEVICES

CROSS-REFERENCE TO RELATED APPLICATION

The present application is a continuation-in-part of application Ser. No. 11/305,586 filed on Dec. 16, 2005, now abandoned, which is a continuation-in-part of application Ser. No. 11/196,044 filed on Aug. 2, 2005, pending, which is a continuation-in-Part of U.S. patent application Ser. No. 11/186,029, filed on Jul. 20, 2005, now abandoned, and claims priority to Provisional Application No. 60/610,846, filed on Sep. 16, 2004, now expired.

BACKGROUND OF THE INVENTION

1. Field of the Invention

The present application relates to an aspiration system for a medical aspiration system.

2. Prior Art

The lens of a human eye may develop a cataracteous condition which affects a patients vision. Cataracteous lenses are sometimes removed and replaced in a procedure commonly referred to as phacoemulsification. Phaco procedures are typically performed with an ultrasonically driven hand piece which is used to break the lens. The broken lens is removed through an aspiration line that is coupled to the hand piece.

The hand piece has a tip that is inserted through an incision in the cornea. The hand piece typically contains a number of ultrasonic transducers that convert electrical power into a mechanical oscillating movement of the tip. The distal end of the tip has an opening that is in fluid communication with the aspiration line. The distal end of the tip also has a sleeve which has an opening in fluid communication with an irrigation line. The irrigation line is typically connected to a bottle that can provide irrigation fluid to the surgical site.

The oscillating movement of the tip breaks the lens into small pieces. The lens pieces and irrigation fluid are drawn into the aspiration line through the opening of the tip. When performing a phaco procedure it is essential to maintain a positive pressure within the anterior chamber of the eye. A negative pressure may cause the cornea to collapse. To maintain a positive chamber pressure the system is configured to provide a flow rate through the irrigation tube that is greater than the flow rate through the aspiration tube.

It has been found that the aspiration system may become occluded, especially at the hand piece tip, during a procedure. The occlusion will increase the vacuum pressure within the aspiration line. The increase in pressure may pull the occluded particle through the aspiration system. The surgeon may also break the occluding piece of lens into smaller pieces. When the occlusion is cleared the anterior chamber may be instantaneously exposed to a high vacuum pressure. The vacuum pressure may cause the cornea to collapse.

Occlusions can also be cleared by depressing a reflux bulb attached to the system. The reflux bulb creates a surge of fluid through the system that creates a fluidic force that can dislodge the occlusion.

U.S. Pat. No. 6,478,781 issued to Urich et al. discloses a coiled tube that can be used to minimize pressure surges in an aspiration system. The tube has a length of at least 8 feet and a number of coils that create a fluidic resistance which minimizes vacuum surges. The recited inner diameter of the tube ranges from 0.06 to 0.1 inches, which is industry standard. Although effective, the coiled approach can only account for a limited reduction of the vacuum surge. Additionally, the coil is susceptible to occlusions within the coiled tube.

U.S. Pat. No. 6,599,271 issued to Easley and assigned to Syntec, Inc. discloses an aspiration system that has a flow restrictor and an in-line filter. Likewise, STAAR Surgical of Monrovia, Calif. sells an in-line filter under the name CRUISE CONTROL that contains a flow restrictor. The flow restrictors limit the vacuum surges within the aspiration system.

Conventional phaco procedures are typically performed using a vacuum pressure of about 250 mmHg. There is a desire to increase the vacuum pressure to assist in aspirating larger pieces of the lens. Aspirating larger pieces lowers the amount of ultrasonic work that must be performed on the eye. Lowering the ultrasonic work is desirable because ultrasound can irritate the eye. Consequently, there is a desire to create vacuums up to 500 mmHg to improve aspiration and reduce the amount of ultrasound delivered to the cornea.

In order to achieve effective flow and vacuum surge clamping with flow restrictors, the inner diameter of the restriction must be very small, usually smaller than 0.0010 inch. If lens particles are larger than 0.0010 inch, residues of ultrasonic emulsification or viscous fluids used in surgery escape the filter, and the entire aspiration line can become occluded. Consequently, the filter volume must be large enough to hold all the extracted lens and viscous fluids. The extra amount of fluid added to the aspiration line by the filter increases the compliance of the system which makes the aspiration sluggish. In addition, there is an increased volume of dissolved air which increases the vacuum surge.

Vacuum pressures of 400 mmHg or greater will create turbulent flow in systems that have flow restrictors. The turbulent flow can create air bubbles that become trapped in the filter. When an occlusion occurs the bubbles may create a fluidic spring that generates surges in the system. Additionally, the internal restrictors create a choke point that limits the amount of fluid force created during a reflux cycle. This limits the effectiveness of depressing the reflux bulb to clear an occlusion. It would be desirable to provide a low cost aspiration system that can effectively minimize fluid surges even at relatively high vacuum pressures, and not create a choke point or create turbulent bubbles.

BRIEF SUMMARY OF THE INVENTION

An ophthalmic aspiration system that can be used with a hand piece and a vacuum source, is disclosed and claimed. The system includes a first tube adapted to be attached to the hand piece, a second tube adapted to be attached to the vacuum source, and a filter assembly coupled to the first and second tubes. The second tube has an inner diameter less than an inner diameter of the first tube.

BRIEF DESCRIPTION OF THE DRAWINGS

FIG. 2 is a side view of an in-line filter of the aspiration system;

FIG. 3 is a cross-sectional view of the filter shown in FIG. 2;

FIG. 4 is a side view of an alternate embodiment of the in-line filter; and,

FIG. 5 is a cross-sectional view of the filter shown in FIG. 4;

FIG. 6 is a perspective view of another embodiment of a filter assembly;

FIG. 7 is a cross-sectional view taken at line 6-6 of FIG. 6;

FIG. 8 is an exploded view of the filter assembly.

DETAILED DESCRIPTION

Figure 1:
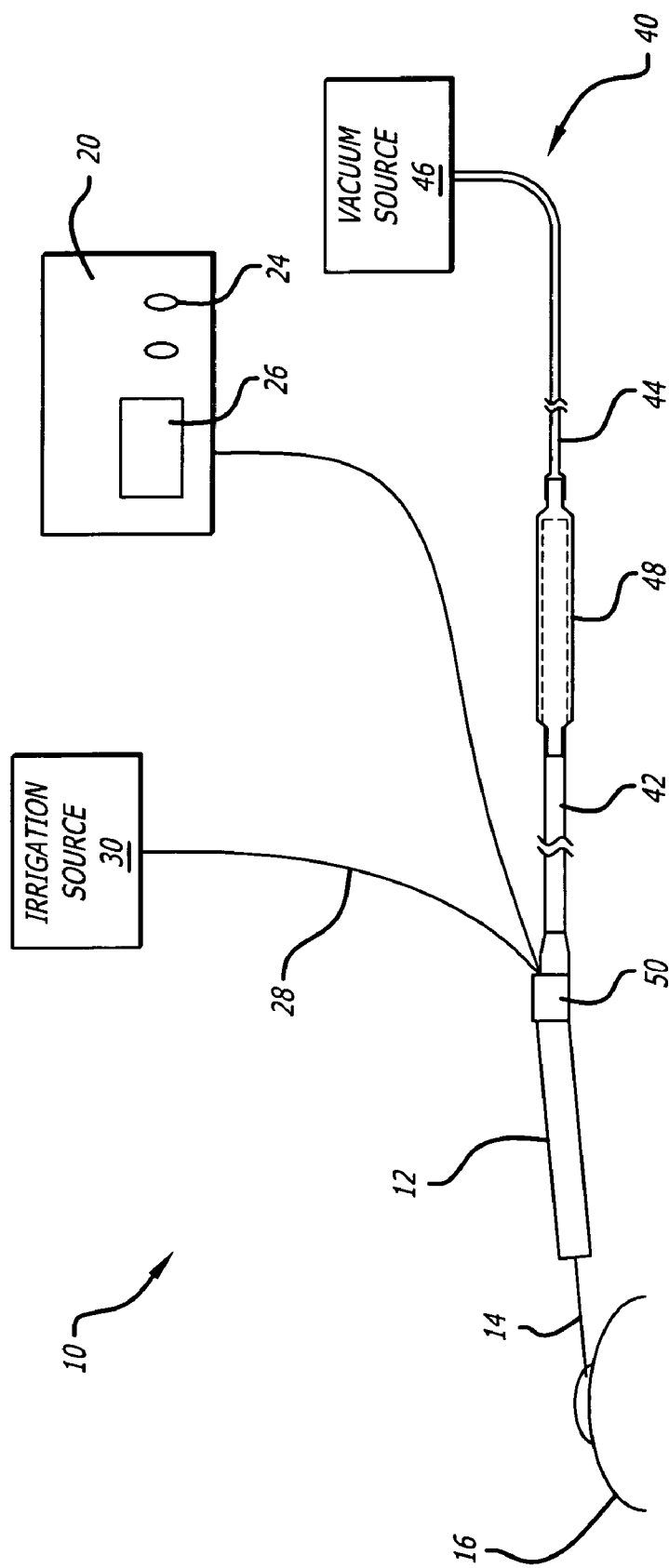
FIG. 1 is an illustration of a medical system with an aspiration system.

Disclosed is an ophthalmic aspiration system that can be used with a hand piece and a vacuum source. The aspiration system includes a first tube that is connected to the hand piece and a second tube that is connected to a vacuum source. A filter assembly is connected to both tubes to filter out particles aspirated into the system. The second tube has an inner diameter smaller than an inner diameter of the first tube. The smaller second tube limits the amount of flow through the system to minimize vacuum surges caused by occlusions.

The filter assembly does not have an internal flow restrictor as found in filters of the prior art. The absence of an internal flow restrictor eliminates a choke point that may restrict a reflux cycle to clear an occlusion. Additionally, internal flow restrictors may create turbulent bubbles at high pressures, a phenomena not found with the disclosed filter assembly.

Referring to the drawings more particularly by reference numbers, FIG. 1 shows an embodiment of a medical system 10. The system 10 may include a hand piece 12 which has a tip 14 that can be inserted into a cornea 16. The tip 14 may also be referred to as a cutting element.

The hand piece 12 may include one or more ultrasonic transducers (not shown) that convert electrical power into mechanical movement of the tip 14. The hand piece 12 is typically held by a surgeon who performs a surgical procedure with the system 10. By way of example, the system 10 can be used to perform a phacoemulsification procedure to break and aspirate a lens of the cornea 16. Although an ultrasonic hand piece 12 is described, it is to be understood that other types of hand pieces or instruments may be used.

The hand piece 12 may be connected to a console 20 of the system 10. The console 20 may provide driving signals to the transducers of the hand piece 12. The console 20 may have input knobs or buttons 24 that allow the surgeon to vary different parameters of the system 10. The console 20 may also have a readout display 26 that provides an indication of the power level, etc. of the system 10.

The system 10 may include an irrigation tube 28 that is connected to the hand piece 12 and an irrigation source 30. The irrigation source 30 may be a bottle that contains an irrigation fluid that flows into the cornea 16 through the irrigation tube 28. The irrigation source 30 may also include a pump to provide a relatively high flow of irrigation fluid to the surgical site. Although the irrigation tube 28 is shown attached to the hand piece 12, it is to be understood that the tube 28 can be inserted directly into the cornea 16.

The medical system 10 may further have an aspiration system 40 that aspirates the irrigation fluid and broken lens out of the cornea 16. The aspiration system 40 may include a first aspiration tube 42 that is connected to the hand piece 12 and a second aspiration tube 44 that is connected to a vacuum source 46. A filter assembly 48 is connected to the first 42 and second 44 aspiration tubes. By way of example, the vacuum source 46 may be a Venturi or Peristaltic type pump.

The aspiration system 40 is in fluid communication with the tip 14. The vacuum pump 46 creates a negative pressure within the aspiration system 40 to induce a flow of fluid and emulsified tissue out of the cornea 16. The pump 46 is configured so that the flow rate through the irrigation tube 28 is slightly greater than the flow rate through the aspiration system 40.

The aspiration system 40 may include a reflux bulb 50 connected to the hand piece 12. The reflux bulb 50 can be squeezed to create a positive pressure and clear an occlusion in the hand piece 12.

As discussed above, internal flow restrictors as found in filters of the prior art may restrict a reflux cycle to clear an occlusion. Because the aspiration system 40 does not include an internal flow restrictor, the aspiration system 40 may include a reflux system at the vacuum source 46 that can be activated to create positive pressure and clear an occlusion in the hand piece 12. The reflux system may be, for example, a bulb system or a silicon tube that is depressed to push fluid through the system. Accordingly, reflux from the vacuum source to the hand piece is much more effective with the current system than with the prior art.

The second aspiration tube 44 has a relatively large fluidic resistance to create a large fluid inertia in the aspiration system 40. The large inertia minimizes instantaneous changes in the flow rate of the irrigation fluid flowing through the aspiration tube 44. Thus if an occlusion is cleared, the large fluidic resistance of the tube 44 will restrict the variation in aspiration fluid flow and minimize the probability of a cornea collapse event.

The second aspiration tube 44 has a diameter less than 0.05 inches and a length of at least 3 feet. By way of example, the tube 44 may have a diameter of 0.04 or 0.035 inches, and a length of 6 feet. The tube inner diameter may have a lower limit of 0.01 inches to ensure flow of emulsified lens tissue. It is desirable to create a fluidic resistance that causes a pressure drop approximately equal to the maximum vacuum pressure of the pump. This will minimize the change in flow rate within the aspiration system in the event a maximum pressure occurs because of an occlusion.

By way of example, most ophthalmic systems are constructed to allow for a maximum aspiration free flow rate of 50 or 60 cc/min. The flow rate is less than the infusion rate, typically 60 to 100 cc/min, to insure a positive pressure in the cornea. A flow rate greater than these values may cause a negative pressure in the cornea. Therefore it is desirable to have an aspiration system that does not allow for a flow rate greater than 50 or 60 cc/min at a vacuum pressure of at least 400 mmHg. Many conventional vacuum pumps can create a maximum pressure of 500 mmHg. Thus the second aspiration tube 44 should have a fluidic resistance that does not allow for a flow rate greater than 50 cc/min at a vacuum pressure of 500 mmHg.

By way of example, when using a Venturi pump set to a vacuum pressure of 150 mmHg or higher, the second tube 44 should produce a pressure drop of at least 150 mmHg and a flow no greater than 60 cc/min. If using a Peristaltic pump set at a pump flow of 40 cc/min or higher the second tube 44 should produce a pressure drop of at least 150 mmHg and a flow no more than 60 cc/min.

Table I provides results of a test using 3 different tube samples. All 3 samples had a length of 6 feet. One of the samples was a conventional prior art aspiration tube having an inner diameter of 0.06 inches. The other tube samples had inner diameters of 0.04 and 0.035 inches, respectively. A vacuum pressure of 500 mmHg was applied for each sample. As shown by Table I, the 0.06 inch tube allowed a flow rate of 230 cc/min, which far exceeds the maximum value of 50-60 cc/min. The 0.04 and 0.35 inch tubes allowed flow rates below the maximum flow rate.

TABLE I

| Tubing Diameter (inch) | Tubing Length (feet) | Flow Limit (cc/min) | Pressure Drop (mmHg) |
|---|---|---|---|
| 0.060 | 6.0 | 230 | 500 |
| 0.040 | 6.0 | 45 | 500 |
| 0.035 | 6.0 | 27 | 500 |

As shown by the results in Table I, the aspiration tubes below 0.05 inches created enough fluidic resistance to prevent excessive fluid flow even at a vacuum pressure of 500 mmHG.

FIGS. 2 and 3 show an embodiment of an in-line filter assembly 48. The in-line filter 48 may include a filter mesh 60 located within a filter housing 62. The filter housing 62 may be roughened to reduce the adhesion of air bubbles to the inner wall of the housing. By way of example the inner wall of the housing 62 may have a roughness between 5 to 500 microns. The filter assembly 48 may have a fluid volume ranging from 0.25 to 5 cc. The housing 62 may include integral luers 64 and 66 that are connected to the first 42 and second 44 aspiration tubes (not shown), respectively. The filter mesh 60 may initially be a flat sheet that is bent and pushed into the filter housing 62 to create a U-shape filter. The mesh 60 should have a sufficient width so that the ends of the sheet overlap. The overlap insures that there are no spaces or holes in the mesh when assembled into the housing.

The filter housing 62 may have longitudinal grooves 67 as shown in FIG. 3 that allow fluid to flow through the filter assembly when particles fill the inner chamber 68 of the filter mesh.

FIGS. 4 and 5 show an alternate embodiment of a filter assembly 70. The assembly includes a filter mesh 72 inside a filter housing 74. The housing 74 may have luers 76 and 78 connected to the tubes 42 and 44 (not shown), respectively. The housing 74 may be roughened and have a fluid volume the same or similar to the filter described and shown in FIGS. 2 and 3.

The filter mesh 72 may include a pair of ears 80 that create channels 82 between the mesh 72 and the filter housing 74. The channels 82 allow for fluid to flow even when particles are being captured by the filter mesh 72.

FIGS. 6-8 show another embodiment of a filter assembly 100, and tubes 102 and 104. The filter assembly 100 may include a mesh 106 located within a filter housing 108. The mesh 106 may be constructed from a flat piece of white nylon mesh material having 0.0118 inch openings. The flat mesh material may be folded and sealed along three sides, leaving one side 111 open to allow particles to flow into the mesh. The mesh may be sealed by heating the edges of the mesh material. Alternatively, the filter can be constructed from two separate sheets of mesh material that are aligned and sealed along three edges.

The filter housing 108 may be constructed from an acrylic material with an inner diameter of 0.173 inches. The flat sealed mesh may have a width of 0.239 inches, wider than the inner diameter of the housing 108. The flat mesh is pushed into the filter housing 108. The smaller inner diameter of the housing 108 causes the mesh 106 to expand into an oblong shape as shown in FIG. 7. The oblong shape of the filter mesh 106 creates channels 110 between the mesh and the inner surface of the housing 108. The channels 110 allow fluid to flow between the mesh and housing wall even while particles are within the mesh.

A cap 112 may be attached to the filter housing 108 to enclose the filter mesh. The cap 112 may be constructed from an acrylic material and glued to the housing 108 with an adhesive such as Loctite 4601. The inner passage diameter of the cap 112 and the output port 114 of the cartridge may each have a diameter of 0.070 inches. The inner surface of the filter housing 108 may have a roughness of GAR G-6 as defined by equipment provided by GAR Electroformers, Inc, of Danbury Conn. This roughness may reduce the adhesion of air bubbles to the wall of the housing 108.

The first tube 102 can be attached to the cap 112. The first tube 102 can be constructed from conventional tubing material used in aspiration systems. The second tube 104 is connected to the filter housing 108. The second tube 104 may be constructed from a PVC material having a 74 durometer. The inner diameter of the tube 104 may be 0.040 inches and the outer diameter may be 0.125 inches. The second tube 104 can be assembled by initially placing the tube 104 onto a tool (not shown). The tool 104 expands the second tube 104 so that the tube can be inserted onto the filter housing 108. The tube contracts to create a friction fit onto the output port 114 of the housing 108.

The aspiration system 40 can filter particles and minimize vacuum surges without introducing complicated parts or increased costs to the system.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An ophthalmic aspiration system that can be used with a hand piece and a vacuum source, comprising:
   a first tube adapted to be attached to the hand piece, said first tube having a first inner diameter;
   a second tube adapted to be attached to the vacuum source, said second tube having a second inner diameter that is smaller than said first inner diameter of said first tube; and,
   a filter assembly coupled to said first and second tubes;
   wherein said second tube has an inner diameter less than 0.05 inches, and said second tube has a length of at least 3 feet.

2. An ophthalmic aspiration system that can be used with a hand piece and a vacuum source, comprising:
   a first tube adapted to be attached to the hand piece, said first tube having a first inner diameter;
   a second tube adapted to be attached to the vacuum source, said second tube having a second inner diameter that is smaller than said first inner diameter of said first tube; and,
   a filter assembly coupled to said first and second tubes;
   wherein said second tube has an inner diameter less than 0.05 inches;
   wherein said filter assembly includes a filter located within a filter housing; and
   wherein said filter housing has an inner surface with a surface roughness of GAR G-6.

3. The system of claim 2, wherein said filter has a shape that creates a channel between said filter and said filter housing.

4. An ophthalmic system, comprising:
   a hand piece;
   a vacuum source;
   a first tube connected to said hand piece, said first tube having a first inner diameter;
   a second tube connected to said vacuum source, said second tube having a second inner diameter that is smaller than said first inner diameter of said first tube; and,
   a filter assembly coupled to said first and second tubes;
   wherein said second tube has an inner diameter less than 0.05 inches, and said second tube has a length of at least 3 feet.

5. The system of claim 4, wherein said vacuum source generates a vacuum of at least 250 mmHg.

6. The system of claim 4, further comprising an irrigation source to provide irrigation fluid that is aspirated by said vacuum source.

7. An ophthalmic system, comprising:
a hand piece;
a vacuum source;
a first tube connected to said hand piece, said first tube having a first inner diameter;
a second tube connected to said vacuum source, said second tube having a second inner diameter that is smaller than said first inner diameter of said first tube; and,
a filter assembly coupled to said first and second tubes;
wherein said second tube has an inner diameter less than 0.05 inches;
wherein said filter assembly includes a filter located within a filter housing; and
wherein said filter housing has an inner surface with a surface roughness of GAR G-6.

8. The system of claim 7, wherein said filter has a shape that creates a channel between said filter and said filter housing.

9. An ophthalmic aspiration system that can be used with a hand piece and a vacuum source, comprising:
a first tube adapted to be attached to the hand piece, said first tube having a first inner diameter;
a second tube adapted to be attached to the vacuum source, said second tube having a second inner diameter that is smaller than said first inner diameter of said first tube; and,
a filter assembly coupled to said first and second tubes;
wherein said second tube has an inner diameter less than 0.05 inches;
wherein said filter assembly includes a filter located within a filter housing; and
wherein said filter has a shape that creates a channel between said filter and said filter housing; and
wherein said filter has an oblong shape within said filter housing.

10. The system of claim 9, wherein the second tube is attached to said filter housing.

11. The system of claim 9, wherein said filter comprises a mesh material that includes a plurality of 0.0118 inch openings.

12. The system of claim 9, wherein said filter housing has a volume of at least 0.25 cc but no more than 5 cc.

13. An ophthalmic aspiration system that can be used with a hand piece and a vacuum source, comprising:
a first tube adapted to be attached to the hand piece, said first tube having a first inner diameter;
a second tube adapted to be attached to the vacuum source, said second tube having a second inner diameter that is smaller than said first inner diameter of said first tube; and,
a filter assembly coupled to said first and second tubes;
wherein said second tube has an inner diameter less than 0.05 inches;
wherein said filter assembly includes a filter located within a filter housing; and
wherein said filter has a shape that creates a channel between said filter and said filter housing; and
wherein the filter comprises a mesh material sealed on three sides and the filter assembly includes a cap attached to said filter housing.

14. The system of claim 13, wherein the filter comprises an oblong shaped sealed folded piece of mesh material with channels between the oblong sealed folded piece of mesh material and the filter housing.

15. The system of claim 13, wherein all of the mesh material of the filter is a single component having material continuity rather than being an assembly of separate pieces of mesh material.

16. The system of claim 13, wherein the mesh material of the filter is an assembly of at least two separate pieces of mesh material.

* * * * *